US010849991B2

(12) United States Patent
Michalakis et al.

(10) Patent No.: US 10,849,991 B2
(45) Date of Patent: Dec. 1, 2020

(54) GENE THERAPY FOR THE TREATMENT OF A DISEASE OF RETINAL CONE CELLS

(71) Applicant: EyeServ GmbH, Tuebingen (DE)

(72) Inventors: Stylianos Michalakis, Munich (DE); Martin Biel, Starnberg (DE); Mathias Seeliger, Rottenburg (DE)

(73) Assignee: EyeServ GmbH, Tübingen (DE)

( * ) Notice: Subject to any disclaimer, the term of this patent is extended or adjusted under 35 U.S.C. 154(b) by 12 days.

(21) Appl. No.: 16/109,627

(22) Filed: Aug. 22, 2018

(65) Prior Publication Data

US 2018/0353619 A1 Dec. 13, 2018

Related U.S. Application Data

(63) Continuation of application No. PCT/EP2017/054229, filed on Feb. 23, 2017.

(30) Foreign Application Priority Data

Feb. 23, 2016 (WO) ................. PCT/EP2016/053753

(51) Int. Cl.
*C12N 15/63* (2006.01)
*A61K 48/00* (2006.01)
*C07K 14/705* (2006.01)
*A61P 27/02* (2006.01)

(52) U.S. Cl.
CPC ...... *A61K 48/0058* (2013.01); *A61K 48/0066* (2013.01); *A61K 48/0075* (2013.01); *C07K 14/705* (2013.01); *A61P 27/02* (2018.01); *C12N 2750/14143* (2013.01); *C12N 2799/025* (2013.01); *C12N 2830/008* (2013.01)

(58) Field of Classification Search
None
See application file for complete search history.

(56) References Cited

FOREIGN PATENT DOCUMENTS

| WO | 2012094560 A2 | 7/2012 | |
|---|---|---|---|
| WO | 2013063601 A1 | 5/2013 | |
| WO | WO-2013063601 A1 * | 5/2013 | ........... A61K 48/005 |
| WO | 2014186160 A1 | 11/2014 | |

OTHER PUBLICATIONS

Xiong et al in "AAV cis-regulatory sequences are correlated with ocular toxicity" (PNAS Mar. 19, 2019 vol. 116, No. 12, pp. 5785-5794) (Year: 2019).*
Banin et al ("Gene Augmentation Therapy Restores Retinal Function and Visual Behavior in a Sheep Model of CNGA3 Achromatopsia" (Molecular Therapy, Sep. 2015, vol. 23, No. 9, pp. 1423-1433; IDS reference). (Year: 2015).*
Dyka et al "Cone Specific Promoter for Use in Gene Therapy of Retinal Degenerative Diseases" (Advances in Experimental Medicine and Biology published Jan. 1, 2014; IDS reference). (Year: 2014).*
Biel et al. (1999) "Selective loss of cone function in mice lacking the cyclic nucleotide-gated channel CNG3," Proc. Natl. Acad. Sci. USA, 96(13):7553-7557.
Choi et al. (2007) "Production of recombinant adeno-associated viral vectors for in vitro and in vivo use," Current Protocols in Molecular Biology, pp. 16.25.1-16.25.24.
Clark et al. (2002) "Recent advances in recombinant adeno-associated virus vector production," Kidney International, vol. 61, Sympsosium 1, pp. S9-S15.
Grieger et al. (2005) "Adeno-associated virus as a gene therapy vector: Vector development, production, and clinical applications," Adv. Biochem. Engin./Biotechnolo., 99:119-145.
Heilbronn et al. (2010) "Viral Vectors for Gene Transfer: Current Status of Gene Therapeutics," in M. Schafer-Korting (Ed.), Drug Delivery, Handbook of Experimental Pharmacology, 197:143-170.
Howarth et al. (2010) "Using viral vectors as gene transfer tools," Cell Biol. Toxicol., 26:1-20.
Komaromy et al. (2010) "Gene therapy rescues cone function in congenital achromatopsia," Human Molecular Genetics, 19(13):2581-2593.
Li et al. (2002) "Retinoic Acid Upregulates Cone Arrestin Expression in Retinoblastoma Cells through a Cis Element in the Distal Promoter Region," IOVS, 43(5):1375-1383.
Michalakis et al. (2010) "Restoration of cone vision in the CNGA3-/- mouse model of congenital complete lack of cone photoreceptor function," Molecular therapy: The Journal of the American Society of Gene Therapy, 18(12):2057-2063.
Pang et al. (2013) "AAV-mediated gene therapy restores cone function in the Cnga3/Nrl double knockout mouse," Invest. Ophthalmol. Vis. Sci., vol. 54, Meeting Abstract, 2 pages.
Wissinger et al. (1997) "Cloning, chromosomal localization and functional expression of the gene encoding the alpha-subunit of the cGMP-gated channel in human cone photoreceptors," European Journal of Neuroscience, 9:2512-2521.
Ye et al. (2016) "Cone-specific promoters for gene therapy of achromatopsia and other retinal diseases," Human Gene Ther., 46 pages.
Zanta-Boussif et al. (2009) "Validation of a mutated PRE sequence allowing high and sustained transgene expression while abrogating WHV-X protein synthesis: application to the gene therapy of WAS," Gene Therapy, 16:605-619.
Zolotukhin et al. (2002) Production and purification of serotype 1, 2, and 5 recombinant adeno-associated viral vectors, Methods, 28:158-167.
International Preliminary Report on Patentability and Written Opinion for International Patent Application No. PCT/EP2016/053753, dated Aug. 28, 2018, 7 pages.

(Continued)

*Primary Examiner* — Catherine S Hibbert
(74) *Attorney, Agent, or Firm* — Lathrop GPM LLP; James H. Velema, Esq.

(57) ABSTRACT

The present invention relates to a polynucleotide configured for the treatment of a disease of retinal cone cells, such as achromatopsia, a nucleic acid vector comprising said polynucleotide, a pharmaceutical composition comprising said nucleic acid vector, a kit comprising said polynucleotide or said nucleic acid vector, a method of making said nucleic acid vector, and a method for treating a disease of the retinal cone cells.

32 Claims, 6 Drawing Sheets

Specification includes a Sequence Listing.

(56) References Cited

OTHER PUBLICATIONS

Banin et al., Sep. 2015, "Gene Augmentation Therapy Restores Retinal Function and Visual Behavior in a Sheep Model of CNGA3 Achromatopsia", Molecular Therapy, vol. 23, No. 9, pp. 1423-1433.
Carvalho et al., May 2011, "Long-term and age-dependent restoration of visual function in a mouse model of CNGB3-associated achromatopsia following gene therapy", Human Molecular Genetics, vol. 20, No. 16, pp. 3161-3175.
Pang et al., Apr. 2012, "AAV-Mediated Cone Rescue in a Naturally Occurring Mouse Model of CNGA3-Achromatopsia", PLOS One, vol. 7, Issue 4, pp. 1-9.
Dyka et al., Jan. 2014, "Cone Specific Promoter for Use in Gene Therapy of Retinal Degenerative Diseases", Adv Exp Med Biol., vol. 801, pp. 1-9.
Du et al., Apr. 2015, "Vitreal delivery of AAV vectored Cnga3 restores cone function in CNGA3-/-/Nrl-/- mice, an all-cone model of CNGA3 achromatopsia", Human Molecular Genetics, vol. 24, No. 13, pp. 3699-3707.
Komaromy et al., Jul. 2008, "Targeting gene expression to cones with human cone opsin promoters in recombinant AAV", Gene Therapy, vol. 15, No. 14, pp. 1049-1055.
May 2, 2017, International Search Report and Written Opinion for International Patent Application No. PCT/EP2017/054229, 17 pages.

* cited by examiner

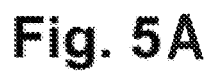
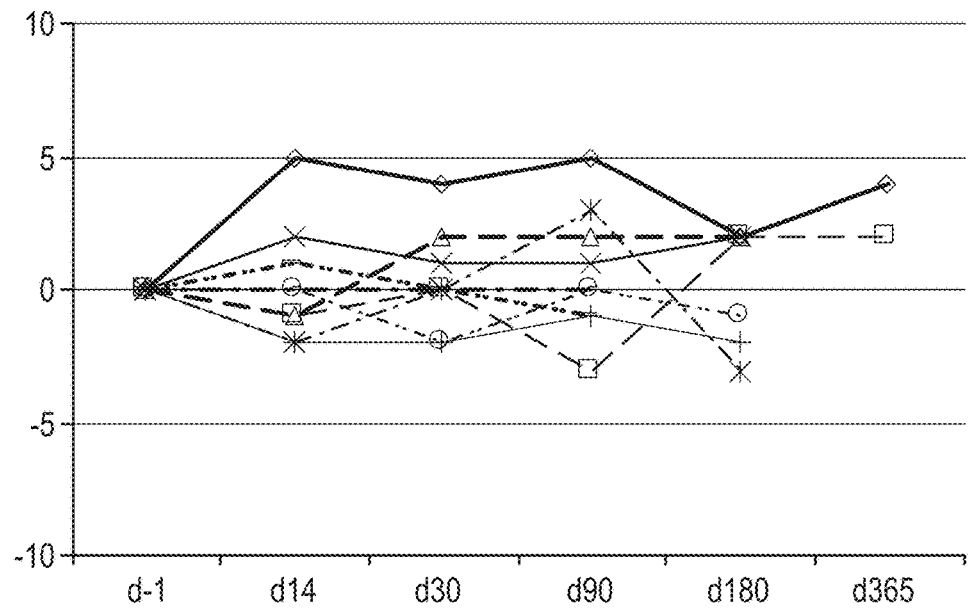
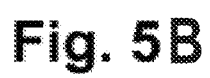
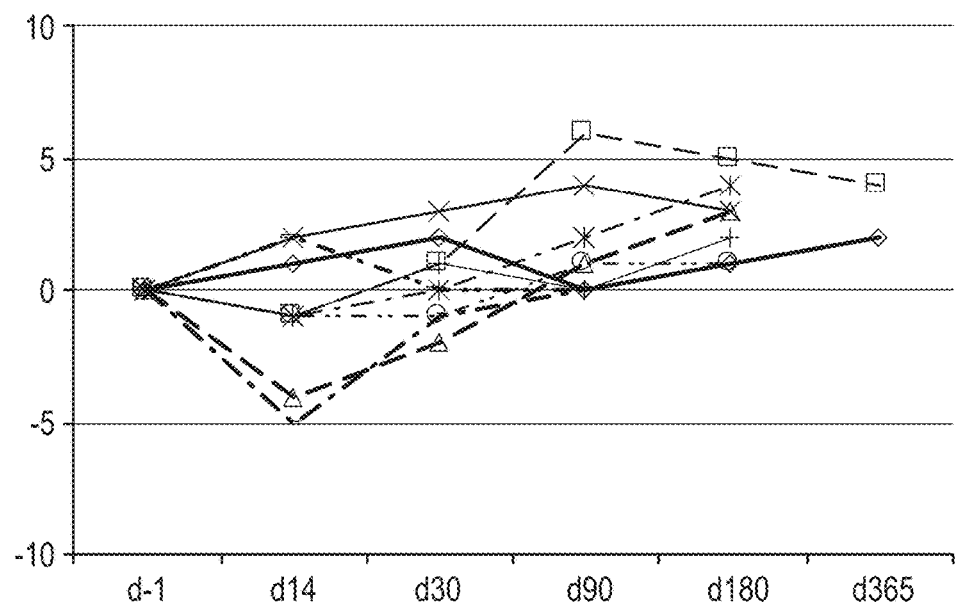

before treatment after treatment

GENE THERAPY FOR THE TREATMENT OF A DISEASE OF RETINAL CONE CELLS

CROSS-REFERENCES TO RELATED APPLICATIONS

This application is a continuation of copending International Patent Application PCT/EP2017/054229 filed on 23 Feb. 2017 and designating the United States of America, and claims priority of International Patent Application PCT/EP2016/053753 filed on 23 Feb. 2016, which is incorporated herein by reference.

REFERENCE TO A SEQUENCE LISTING

This application contains references to amino acid sequences and nucleic acid sequences which have been submitted concurrently herewith as the sequence listing text file "1884P100WO.txt", file size 18.5 Kilobytes (KB), created on 10 Aug. 2018. The aforementioned sequence listing is hereby incorporated by reference in its entirety pursuant to 37 C.F.R. § 1.52(e)(5).

FIELD

The present invention relates to a polynucleotide configured for the treatment of a disease of retinal cone cells, such as achromatopsia, a nucleic acid vector comprising said polynucleotide, a pharmaceutical composition comprising said nucleic acid vector, a kit comprising said polynucleotide or said nucleic acid vector, a method of making said nucleic acid vector, and a method for treating a disease of the retinal cone cells.

BACKGROUND

Inherited retinal dystrophies are chronic and disabling disorders of visual function. Achromatopsia (ACHM) is a specific form thereof. ACHM is characterized by reduced visual acuity, pendular nystagmus, increased sensitivity to light (photophobia), a small central scotoma, eccentric fixation, and reduced or complete loss of color discrimination. All individuals with ACHM, so-called achromats, have impaired color discrimination along all three axes of color vision corresponding to the three cone classes: the protan or long-wavelength-sensitive cone axis (red), the deutan or middle-wavelength-sensitive cone axis (green), and the tritan or short-wavelength-sensitive cone axis (blue). Most individuals have complete ACHM, with total lack of function of all three types of cones. Rarely, individuals have incomplete ACHM, in which one or more cone types may be partially functioning. The symptoms are similar to those of individuals with complete ACHM, but generally less severe.

ACHM is estimated to affect 1 in 40,000 live births worldwide. It is inherited in an autosomal recessive manner. At conception, each sib of an affected individual has a 25% chance of being affected, a 50% chance of being an asymptomatic carrier, and a 25% chance of being unaffected and not a carrier. Carrier testing for at-risk relatives and prenatal testing for pregnancies at increased risk are possible if the pathogenic variants have been identified in the family.

There are various genetic causes of inherited ACHM. Currently mutations in the following genes have been implicated in ACHM: cone cyclic nucleotide-gated channel alpha 3 [CNGA3] and beta 3 subunit [CNGB3], guanine nucleotide binding protein (G protein) alpha transducing activity polypeptide 2 [GNAT2], phosphodiesterase 6C, CGMP-specific, cone, alpha prime [PDE6C], and phosphodiesterase 6H, CGMP-specific, cone, gamma [PDE6H], AFT6.

The most common cause of ACHM in the western population is mutations in the two genes CNGA3 and CNGB3. CNGB3 (ACHM type 1, ACHM1) mutations are found in ca. 50% of cases, and CNGA3 (ACHM2) mutations in about 28% of patients. Mutations in CNGA3 are the most common cause of ACHM in Chinese, Middle East and Arabic populations accounting for up to 60% of ACHM cases. The frequency in other genes involved in ACHM, such as guanine nucleotide binding protein (G protein) alpha transducing activity polypeptide 2 [GNAT2], phosphodiesterase 6C, CGMP-specific, cone, alpha prime [PDE6C] and phosphodiesterase 6H, CGMP-specific, cone, gamma [PDE6H], and AFT6, is very low and below 1.5%, respectively.

In general, the molecular pathomechanism of ACHM is either the inability to properly control or respond to altered levels of cGMP. cGMP is particularly important in visual perception as its level controls the opening of cyclic nucleotide-gated ion channels (CNGs). Decreasing the concentration of cGMP results in closure of CNGs and resulting hyperpolarization and cessation of glutamate release. Native retinal CNGs are composed of 3 α- and 1 β-subunits, which are CNGA3 and CNGB3, respectively, in cone cells.

Due to the genetic nature of inherited retinal dystrophies like ACHM conventional treatments are not applicable. The burden of disease is so severe that clinical experts put ACHM currently on top of their list of candidates for such therapy.

At present, there is no treatment available for CNGA3-linked achromatopsia (ACHM2).

RELATED PRIOR ART

Komaromy et al., Gene therapy rescues cone function in congenital achromatopsia, Human Molecular Genetics, 19(13): 2581-2593 (2010), describe studies in dogs suggesting some promise for the use of recombinant adeno-associated virus (rAAV)-based gene therapy for the treatment of ACHM caused by mutations in the CNGB3 gene. In the canine studies, the rAAV vectors used packaged a human CNGB3 (hCNGB3) expression cassette that contained a 2.1 kb cone red opsin promoter (PR2.1) and a human CNGB3 (hCNGB3) cDNA. One limitation of the studies was that the hCNGB3 driven by the PR2.1 promoter was expressed only in red and green cones, whereas endogenous hCNGB3 is expressed in all three types of cones (red, green and blue cones). Another limitation was that the overall size of the expression cassette utilized (5,230 bp) was well beyond the normal packaging capacity (<4.9 kb) of AAV particles; the over-stuffed rAAV particles dramatically impaired the rAAV packaging efficiency, resulting in low yields, a higher empty-to-full particle ratio, and likely a lower infectivity of the vector.

WO 2012/094560 describes rAAV-based vectors comprising the hCNGA3 coding sequence under the control of specific short promoters comprising 5'-NTR sections of the CNGB3 gene and a cytomegalovirus (CMV) enhancer. According to the authors the shortness of the promoters would allow the hCNGB3 expression cassette to fit within the normal packaging capacity of rAAV allegedly resulting in several benefits, such as improved yields, a lower empty-to-full particle ratio, and higher infectivity of the vector. However, the inventors were not able to verify these features.

Pang et al., AAV-mediated gene therapy restores cone function in the Cnga3/Nrl double knockout mouse, Invest.

Ophthalmol. Vis. Sci. 54, Meeting Abstract, 2723 (2013), describe an rAAV5 vector comprising the coding sequence of the hCNGA3 gene. The vector was injected into the eye of Cnga3/Nrl double knockout (Cnga3/Nrl DKO) mice. The authors mention that the cone degeneration in the treated mice was stopped. However, according to the inventors in this approach the yield of gene replacement is not satisfactory suggesting that this strategy might be less promising for the treatment of humans suffering from inherited retinal dystrophies like ACHM.

Ye et al., Cone-specific promoters for gene therapy of achromatopsia and other retinal diseases, Hum. Gene Ther. 27, 72-82 (2016), disclose an AAV vector expressing a human CNGB3 gene driven by a 1.7-kb L-opsin promoter (PR1.7). Subretinal injection of said vector into CNGB3-deficient mice partially rescued the cone function. However, even though suggested by the authors so far a clinical use of this vector has not proven successful.

Dyka et al., Cone specific promotor for use in gene therapy of retinal degenerative diseases, in: Ash et al. (Ed.) et al., Retinal Diseases—Mechanisms and Experimental Therapy, Chapter 87, 695-701 (2014), describe several cone specific promoters. A reasonable strategy for the treatment of inherited retinal dystrophies like ACHM is, however, not provided.

SUMMARY

Against this background it is an object of the present invention to provide a polypeptide and a nucleic acid vector which address these limitations and, therefore, will be valuable tools in the treatment of a disease of the retinal cone cells, such as ACHM, in particular ACHM2.

This object is met by a polynucleotide, comprising a transgene expression cassette, said transgene expression cassette comprises (a) a nucleic acid encoding the promoter of human retinal arrestin 3 gene (hArr3), (b) a nucleic acid encoding the human cone cyclic nucleotide-gated channel alpha 3 subunit (hCNGA3) or fragments thereof, and (c) a nucleic acid encoding regulatory elements.

The inventors were able to realize that the polynucleotide of the invention embodies the essential components of a genetic tool allowing a successful therapy of a disease of the retinal cone cells, such as ACHM, which can be applied to a human patient.

It was experimentally demonstrated by the inventors that CNGA3-deficient mice which received a subretinal injection of the polynucleotide according to the invention as a component of a vector plasmid express the hCNGA3 transgene efficiently and specifically in the cone photoreceptor cells. In addition, it was demonstrated that cone-mediated vision was conferred to these mice that lack cone function from birth.

This finding was surprising. It was not rendered obvious by the art that a polynucleotide having a structure as suggested by the invention would result in a targeted hCNGA3 transgene expression in the retina. Actually, the contrary was expected. The art explicitly advises against the solution provided by the invention.

Dyka et al. (l.c.) describe that mouse and human cone arrestin promoters when used with the intention to express in the retina such genes which are involved in the pathology of ACHM, a low target tissue specificity will occur.

In WO2012/094560 (l.c.) it is asserted that expression cassettes encoding retinal CNGs which are under the control of a cone arrestin promoter will be little effective in restoring visual function.

The same is taught by Komaromy et al. (l.c.).

Therefore, the observed high specificity and selectivity as well as the significant biological effectivity of the polynucleotide of the invention in restoring the visual function were not self-evident for a person skilled in the art.

As demonstrated by the inventors in primate experiments after being injected into the retina the polynucleotide of the invention will remain in situ with only minimal transduction of off-target organs. It was also found that after the injection into the retina of the polynucleotide of the invention no induction of anti-drug antibodies against the administered polynucleotide will occur. Finally, it was experimentally found that the polynucleotide of the invention can be successfully delivered to the retinal cone photo receptor cells of human patients with CNGA3 based ACHM via an appropriate rAAV vector. This allows the conclusion that the polynucleotide of the invention is well suited as an active agent of a pharmaceutical composition for the treatment of a disease of retinal cone cells, such as ACHM.

According to the invention, a "polynucleotide" is a biopolymer molecule composed of 13 or more nucleotide monomers covalently bonded in a chain. An example of a preferred polynucleotide is a DNA molecule. While the polynucleotide according to the invention may be single-stranded or double-stranded, in a preferred embodiment the polynucleotide is single-stranded.

A "promoter" is a region of DNA that facilitates the transcription of a particular gene. As part of the process of transcription, the enzyme that synthesizes RNA, known as RNA polymerase, attaches to the DNA near a gene. Promoters contain specific DNA sequences and response elements that provide an initial binding site for RNA polymerase and for transcription factors that recruit RNA polymerase.

The promoter of the human retinal arrestin 3 gene (hArr3) refers to the region of DNA that facilitates the transcription of human arrestin 3, retinal (X-arrestin). The entire nucleotide sequence of the promotor of hArr3 is disclosed in Li et al., Retinoic acid upregulates cone arrestin expression in retinoblastoma cells through a Cis element in the distal promoter region, Invest. Ophthalmol. Vis. Sci. 43(5): 1375-1383 (2002).

In an embodiment the entire promoter nucleotide sequence is employed. In another embodiment of the invention only functional parts of the promotor are used which are required for a targeted expression of the hCNGA3. In still another embodiment of the invention fusions of the before mentioned nucleotide sequences with other promoter nucleotide sequences, intronic sequences or regulatory element sequences are used.

A "transgene expression cassette" or "expression cassette" comprises the gene sequences that a nucleic acid vector is to deliver to target cells. These sequences include the gene of interest (e.g., the hCNGA3 nucleic acid), one or more promoters, and regulatory elements.

"Regulatory elements" are regulatory elements that are necessary for effective expression of a gene in a target cell (e.g., the hCNGA3 nucleic acid), and thus should be included in a transgene expression cassette. Such sequences could include, for example, enhancer sequences, polylinker sequences facilitating the insertion of a DNA fragment within a plasmid vector, or sequences responsible for intron splicing and polyadenylation of mRNA transcripts.

A "nucleic acid" or "nucleic acid molecule" is a molecule composed of chains of monomeric nucleotides, such as, for example, DNA molecules (e.g., cDNA or genomic DNA). A nucleic acid may encode, for example, a promoter, the hCNGA3 gene or a fragment thereof, or regulatory elements. A nucleic acid molecule can be single-stranded or double-stranded.

A "nucleic acid encoding hCNGA3" refers to a nucleic acid that comprises a nucleotide sequence which codes for the human CNGA3 or, in one embodiment of the invention, a fragment or a functional variant of the human CNGA3. A "fragment" of the hCNGA3 refers to a segment or part of the hCNGA3 which still exhibits hCNGA3 activity. A "functional variant" of the hCNGA3 includes a variant of the protein with minor variations such as, for example, silent mutations, single nucleotide polymorphisms, missense mutations, and other mutations or deletions, that do not significantly impair or alter the function of the wild type hCNGA3.

The amino acid sequence of hCNGA3 which is encoded, at least partially, by the "nucleic acid encoding hCNGA3" according to the invention is depicted under SEQ ID No. 3.

The polynucleotide of the invention includes an "isolated" polynucleotide or nucleic acid molecule, respectively, which is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

In an embodiment of the invention said regulatory elements comprise c1) a nucleic acid encoding woodchuck stomatitis virus posttranscriptional regulatory element (WPRE).

This embodiment of the polynucleotide according to the invention has the advantage that the expression of the hCNGA3 in the photoreceptor cells is significantly enhanced. The long term expression that is achieved by the inclusion of WPRE qualifies the polynucleotide for its use in gene therapy. The WPRE contains the woodchuck hepatitis virus X open reading frame (WHX ORF) gene promoter and an open-reading frame coding for the first 61 AA of WHX in its 30 region; see Zanta-Boussif et al., Validation of a mutated PRE sequence allowing high and sustained transgene expression while abrogating WHV-X protein synthesis: application to the gene therapy of WAS, Gene Ther., 16(5), 605-619 (2009).

In another embodiment of the invention in the polynucleotide according to the invention said WPRE is a mutated WPRE (WPREm), comprising a WHX OR of non-expressible WHX protein.

This measure has the advantage that it precludes the non-intended expression of the WHX protein from the expression cassette.

In another embodiment of the invention said regulatory elements comprise (c2) a nucleic acid encoding a polyadenylation signal (pA).

This measure has the advantage that the polynucleotide is provided with such a regulatory element that is important for the nuclear export, translation, and stability of the hCNGA3-encoding mRNA, thereby improving the expression efficiency.

In a further embodiment of the invention said polyadenylation signal is a bovine growth hormone pA (BGH pA).

The inventors have realized that this specific polyadenylation signal ensures especially good results when used in conjunction with the remaining genetic elements of the polynucleotide of the invention.

In another embodiment the polynucleotide of the invention further comprises a nucleic acid encoding inverted terminal repeats (ITRs) flanking said transgene expression cassette, preferably it comprises at least one ITR adjacent to said hArr3 promoter (L-ITR) at the first end of the expression cassette, and at least one ITR adjacent to said pA (R-ITR) at the second end of the expression cassette opposite to the first end.

This measure has the advantage that it allows for efficient replication and packaging during manufacturing. "Flanking" means that the ITRs are located at both sides of the transgene expression cassette, i.e. at the 5' and 3' termini. The ITRs thereby frame the transgene expression cassette.

In an embodiment of the invention said ITRs are derived from Adeno-associated Virus (AAV) serotype 2 (ITR AAV2).

As it could be found this specific ITRs are particularly suited for the polynucleotide of the invention.

In another embodiment of the invention the polynucleotide comprises the following arrangement order: (a)-(b)-(c), preferably (a)-(b)-(c1)-(c2), further preferably (L-ITR)-(a)-(b)-(c1)-(c2)-(R-ITR).

The indicated order of the genetic elements has been proven as beneficial for the expression efficiency of the polynucleotide according to the invention.

In another embodiment of the invention said hArr3 promoter comprises the nucleotide sequence of SEQ ID No. 1, said nucleic acid encoding hCNGA3 comprises the nucleotide sequence of SEQ ID No. 2, said nucleic acid encoding hCNGA3 comprises a nucleotide sequence encoding the amino acid sequence of SEQ ID No. 3, said nucleic acid encoding WPREm comprises the nucleotide sequence of SEQ ID No. 4, said nucleic acid encoding BGH pA comprises the nucleotide sequence of SEQ ID No. 5, said nucleic acid encoding L-ITR comprises the nucleotide sequence of SEQ ID No. 6 and/or said nucleic acid encoding R-ITR comprises the nucleotide sequence of SEQ ID No. 7.

This measure has the advantage that with the specific nucleotide sequences of the respective genetic elements of the polynucleotide according to the invention a precise construction manual is provided. This allows an easy and time-saving synthesis of the polynucleotide, e.g. by means of a nucleic acid synthesizer.

Another subject-matter of the invention is a nucleic acid vector comprising the above-referenced polynucleotide according to the invention. Therefore, the features, advantages and characteristics of the polynucleotide apply likewise to the nucleic acid vector of the invention.

In preferred embodiments, the nucleic acid vector according to the invention is a viral vector, such as a vector derived from an adeno-associated virus, an adenovirus, a retrovirus, a lentivirus, a vaccinia/poxvirus, or a herpesvirus (e.g., herpes simplex virus (HSV)). In the most preferred embodiments, the vector is an adeno-associated viral (AAV) vector (see below).

In an embodiment of the invention the nucleic acid vector is a circular plasmid which further comprises a backbone having a length of 5,000 bp, preferably 5.500 bp.

According to the invention, the term "backbone" refers to the section of the vector molecule beyond the expression cassette or, if present, the inverted terminal repeats (ITRs). In other words, the backbone of the vector is adjacent to the 5' and 3' termini of the expression cassette or ITRs, respectively, and forms the rest of the vector's nucleic acids besides the polynucleotide according to the invention.

The inventors have realized that a backbone of this preferred size will minimize a false or reverse packaging of the backbone into a virus particle, instead of a packaging of the expression cassette. Therefore, this measure ensures that essentially only the hCNGA3 will be available for an expression in the target cell.

In another embodiment of the invention said backbone comprises ≤5 open reading frames (ORFs), preferably ≤4 ORFs, further preferably ≤3 ORFs, further preferably ≤2 ORFs, further preferably ≤1 ORFs, highly preferably ≤0 ORFs.

The inventors have realized that the backbone should be low in ORFs, preferably free in ORFs, besides any selection markers or origins of replication (ORI), if applicable. This measure has the advantage that it will further minimize the possibility for expression of side products in case of reverse packaging. In addition, it minimizes the possibility for expression of side products during manufacturing of rAAV vectors.

In still another embodiment of the nucleic acid vector according to the invention said backbone comprises a selection marker, preferably an antibiotic resistance encoding nucleic acid, further preferably a kanamycin resistance encoding nucleic acid (KanR).

This measure provides for the constructive preconditions allowing the selection of cells in vitro which incorporate the nucleic acid vector. Such cells may be used to amplify the vector.

In another embodiment of the invention said selection marker of the backbone of the nucleic acid vector is at its 5' and 3' termini remotely spaced apart from the polynucleotide, preferably maximally remotely spaced apart from the polynucleotide or expression cassette, further preferably ≥1,000 bp, further preferably ≥1,500 bp, highly preferably ≥1,900 bp spaced apart from the polynucleotide or expression cassette according to the invention.

As the inventors have realized this measure has the advantage that the resistance encoding nucleic acid (KanR) is maximally spaced apart from the ITRs and regulatory elements of the expression cassette, e.g. the promoter.

In a further development of the nucleic acid vector the backbone comprises ≤10 restriction enzyme recognition sites (RERSs), preferably ≤5 RERSs, further preferably ≤3 RERSs, further preferably ≤2 RERSs, further preferably ≤1 RERSs, highly preferably 0 RERSs.

This measure has the advantage that the stability of the nucleic acid vector in bacteria used for DNA amplification is significantly increased.

In a further development of the nucleic acid vector according to the invention the backbone comprises ≤5 promoters, preferably ≤4 promoters, further preferably ≤3 promoters, further preferably ≤2 promoters, further preferably ≤1 promoters, highly preferably 0 promoters.

This measure further minimizes the possibility for expression of side products in case of reverse packaging which may cause adverse effects or interference with the transgene. In this embodiment "promoters" are to be understood as excluding the promoter necessary for expressing the selection marker, e.g. the KanR, which will typically represented by an appropriate prokaryotic promoter.

In a further embodiment of the nucleic acid vector according to the invention said backbone further comprises an origin of replication (ORI), preferably a pUC18 ORI.

This measure provides the structural preconditions for the vector being replicable.

The backbone preferably comprises as the only encoding or information-carrying sequences the selection marker and the ORI, and for the rest random sequences but no ORFs, promoters or RERSs.

The nucleotide sequence comprised by the vector backbone is depicted in the enclosed sequence listing under SEQ ID No. 8.

In a preferred embodiment the nucleic acid vector of the invention is an adeno-associated viral (AAV) vector.

Multiple serotypes of adeno-associated virus (AAV), including 12 human serotypes (AAV1, AAV2, AAV3, AAV4, AAV5, AAV6, AAV7, AAV8, AAV9, AAV10, AAV11, and AAV12) and more than 100 serotypes from nonhuman primates have now been identified. Howarth et al., Using viral vectors as gene transfer tools. Cell Biol. Toxicol. 26: 1-10 (2010). The serotype of the inverted terminal repeats (ITRs) or the capsid sequence of the AAV vector may be selected from any known human or nonhuman AAV serotype. In some embodiments a pseudotyping approach is employed, wherein the genome of one ITR serotype is packaged into a different serotype capsid. See e.g., Zolutuhkin et al. Production and purification of serotype 1, 2, and 5 recombinant adeno-associated viral vectors, Methods 28(2): 158-67 (2002).

While any kind of AAV could be used it is further preferred if the serotype of the AAV capsid sequence and/or the inverted terminal repeats (ITRs) of said AAV vector is selected from the group consisting of AAV2, AAV5, AAV8, modifications or combinations thereof.

The inventors have realized that the AAV2, AAV5, AAV8 subtypes are particularly suited for the creation of the nucleic acid vector according to the invention.

The production, purification, and characterization of the recombinant AAV vectors of the present invention may be carried out using any of the many methods known in the art. For reviews of laboratory-scale production methods, see, e.g., Clark, Recent advances in recombinant adeno-associated virus vector production. Kidney Int. 61s:9-15 (2002); Choi et al., Production of recombinant adeno-associated viral vectors for in vitro and in vivo use. Current Protocols in Molecular Biology 16.25.1-16.25.24 (2007); Grieger and Samulski, Adeno-associated virus as a gene therapy vector: Vector development, production, and clinical applications. Adv. Biochem. Engin/Biotechnol 99: 119-145 (2005); Heilbronn and Weger, Viral Vectors for Gene Transfer: Current Status of Gene Therapeutics, in M. Schafer-Korting (Ed.), Drug Delivery, Handbook of Experimental Pharmacology, 197: 143-170 (2010); Howarth et al. (l.c.). The production methods described below are intended as non-limiting examples.

Another subject-matter of the invention is a pharmaceutical preparation comprising the nucleic acid vector as described in detail further above, and a pharmaceutically acceptable carrier. Therefore, the features, advantages and characteristics of the polynucleotide and the nucleic acid vector apply likewise to the pharmaceutical preparation of the invention.

Pharmaceutically acceptable carriers are well known in the art. By way of example, reference is made to Rowe (Ed.) (2012), Handbook of Pharmaceutical Excipients, 6$^{th}$ Edition, Pharmaceutical Press. The pharmaceutical preparation may further contain additives. These include any compound or composition which are advantageous for the effectiveness of the nucleic acid vector according to the invention, such as salts, binders, solvents, dispersants, adjuvants and other substances commonly used in connection in gene therapeutic approaches.

In an embodiment of the pharmaceutical preparation said pharmaceutically acceptable carrier comprises saline solution, preferably balanced sterile saline solution, and optionally a surfactant, preferably micronized poloxamer (Kolliphor® P 188 micro).

The inventors have realized that with such specific formulation drug induced adverse effects and loss of rAAV particles at surfaces are minimized.

In a preferred embodiment the pharmaceutical preparation according to the invention is configured for a use in the treatment of a disease associated with a genetic mutation, substitution, or deletion that affects retinal cone cells, further preferably in the treatment of achromatopsia (ACHM), in particular ACHM type 2 (ACHM2).

With the polynucleotide and the nucleic acid vector described in detail further above the inventors provide a therapeutic tool which, for the first time, allows a causative treatment of CNGA3-linked achromatopsia.

Another subject-matter of the present invention is a kit comprising (a) the polynucleotide according to the invention and/or the nucleic acid according to the invention, and/or the pharmaceutical preparation according to the invention, and (b) instructions for use thereof.

A further subject-matter of the present invention is method of making a recombinant adeno-associated viral (rAAV) vector comprising inserting into an adeno-associated viral vector the polynucleotide according to the invention, preferably said recombinant adeno-associated viral vector is the nucleic acid vector according to the invention.

Another subject-matter of the invention is a method for treating a disease associated with a genetic mutation, substitution, or deletion that affects retinal cone cells, wherein the method comprises administering to a subject in need of such treatment the nucleic acid vector according to the invention and/or the pharmaceutical preparation according to the invention, thereby treating the subject. Preferably the disease is ACHM, further preferably ACHM type 2 (ACHM2). Preferably the vector is administered subretinally and/or intravitreally.

The features, advantages and characteristics of the polynucleotide and the nucleic acid vector apply likewise to the kit, the method of making and the method for treating according to the invention.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention. The features mentioned in the specific embodiments are general features of the invention which are not only applicable in the specific embodiment but also in an isolated manner in the context of any embodiment of the invention.

The invention is now described and explained in further detail by referring to the following figures and non-limiting examples.

BRIEF DESCRIPTION OF THE DRAWINGS

FIGS. 5A-5B show the longitudinal course of best corrected visual acuity (BCVA) after treatment with AAV8.hCNGA3. Upper graph (FIG. 5A) shows data from the treated study eyes, lower graph (FIG. 5B) from the untreated fellow control eyes. Each line represents one patient. BCVA was determined by means of the standardized EDTRS charts under constant illumination. The absolute numbers of letters correctly read by each patient relative to his/her pre-injection baseline (0) are plotted against time (days) after injection. Immediately after injection BCVA drops in most patients but after 180 day every single patient's BCVA has improved in comparison to baseline, indicating a clear tendency of improvement not observed in the control eyes.

EXAMPLES

1. Nucleic Acid Vector of the Invention

Figure 1:
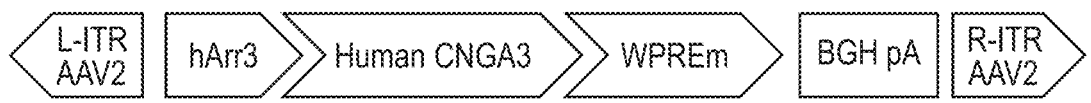
FIG. 1 shows the structure of the rAAV.hCNGA3 vector genome.

In this exemplary embodiment the rAAV.hCNGA3 vector is a hybrid AAV-based vector carrying the cDNA of the human CNGA3 subunit of the cone photoreceptor cyclic nucleotide-gated (CNG) cation channel. The hCNGA3 cDNA expression is under the control of the cone-specific human arrestin 3 (hArr3) promoter and is enhanced using a mutated woodchuck stomatitis virus posttranscriptional regulatory element (WPRE) sequence. The expression cassette is flanked by the AAV serotype 2 inverted terminal repeats (ITRs) and the recombinant genome is packaged in the AAV serotype 8 capsid, resulting in an AAV2/8 hybrid vector. The expression cassette comprises the following elements:

Promoter of the human arrestin 3 (hArr3) gene: 0.4 Kb
cDNA of the human CNGA3 subunit of the cone photoreceptor cyclic nucleotide-gated cation channel: 2 Kb
Woodchuck stomatitis virus posttranscriptional regulatory element (WPRE) with a point mutation in the ATG codon of the WHV-X open reading frame: 0.54 Kb
Polyadenylation signal of the Bovine Growth Hormone (BGH): 0.2 Kb
AAV serotype 2 inverted terminal repeats (ITRs): 0.13 Kb
The structure of the rAAV.hCNGA3 vector genome is depicted in FIG. 1.

2. pGL2.hArr3.hCNGA3.WPREm Cis Vector Plasmid

In one exemplary embodiment the pGL2.hArr3.hCNGA3.WPREm cis vector-plasmid backbone is used that contains an expression cassette comprising a 405 bp cone photoreceptor-specific human cone arrestin (hArr3) promoter [see Li et al, Retinoic acid upregulates cone arrestin expression in retinoblastoma cells through a Cis element in the distal promoter region, Investigative ophthalmology & visual science, 43 (2002) 1375-1383, and Carvalho et al., Long-term and age-dependent restoration of visual function in a mouse model of CNGB3-associated achromatopsia following gene therapy, Human molecular genetics, 20 (2011) 3161-3175] and the full-length (2085 bp) human CNGA3 cDNA [see Wissinger et al., Cloning, chromosomal localization and functional expression of the gene encoding the alpha-subunit of the cGMP-gated channel in human cone photoreceptors]. The expression cassette also contains a 543 bp woodchuck hepatitis virus post-transcriptional regulatory element (WPRE) with mutated WXF-open reading frame [Zanta-Boussif et al., Validation of a mutated PRE sequence allowing high and sustained transgene expression while abrogating WHV-X protein synthesis: application to the gene therapy of WAS, Gene therapy, 16 (2009), 605-619] and a 207 bp bovine growth hormone polyadenylation signal (BGHpA). The 5591 bp vector backbone with the nucleotide sequence depicted in SEQ ID No. 8 containing a kanamycin resistance (KanR) positioned 1943 bp from the L-ITR and 2853 bp from the R-ITR and 2024 bp from a pUC18 ori.

The rAAV.hCNGA3 vector is produced using transient double-transfection of the cis vector plasmid and a trans pDP8-KanR helper plasmid in the human embryonic kidney 293 cells (HEK293). The cell lysate is clarified by a low-speed centrifugation and the vector is then purified by 2 consecutive rounds of cesium chloride gradients ultracentrifugation followed by a tangential flow filtration step for concentration and buffer exchange. The resulting rAAV.hCNGA3 vector suspension is then sterile-filtered and vialed as drug product.

Figure 2A:
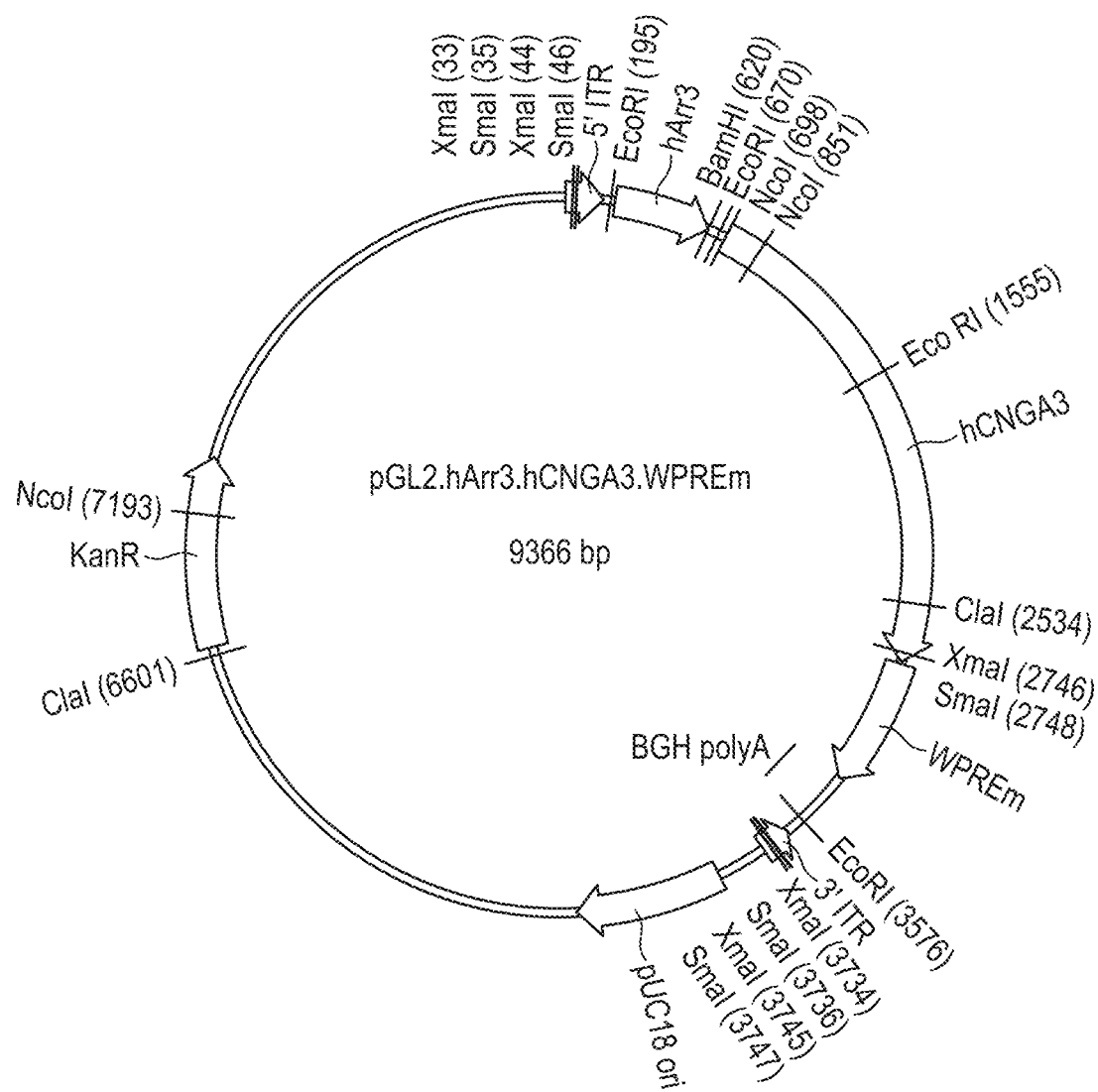
FIGS. 2A-2B show two embodiments of the phArr3.hCNGA3.WPREm cis vector plasmid map.
Figure 2B:

Two embodiments of the phArr3.hCNGA3.WPREm vector plasmid map are shown in FIG. 2A,B.

3. Biological Activity and Transgene Expression Conferred by the rAAV.hCNGA3 Vector To verify biological activity and transgene expression the inventors delivered the rAAV.hCNGA3 vector into the subretinal space of 2-week-old Cnga3-deficient mice [Biel et al., Selective loss of cone function in mice lacking the cyclic nucleotide-gated channel CNG3, Proc Natl Acad Sci USA, 96(13):7553-7557 (1999). The delivery procedure was similar to the one described for the mouse-specific vector [Michalakis et al., Restoration of cone vision in the CNGA3-/- mouse model of congenital complete lack of cone photoreceptor function, Molecular therapy: The Journal of the American Society of Gene Therapy, 18 2057-2063 (2010)]. The mice received a subretinal injection in the treated eye (TE), whereas the other, untreated eye (UE) served as control. The vector efficacy was evaluated at 8 weeks following the injection by means of electroretinography (ERG), an objective functional in vivo assay. Cnga3-deficient mice lack any cone-mediated vision. Therefore, ERG protocols specifically testing for cone function are suitable as an indirect measure for CNGA3 function and for the assessment of biological activity (BAA) of the rAAV.hCNGA3 vector.

Figure 3:
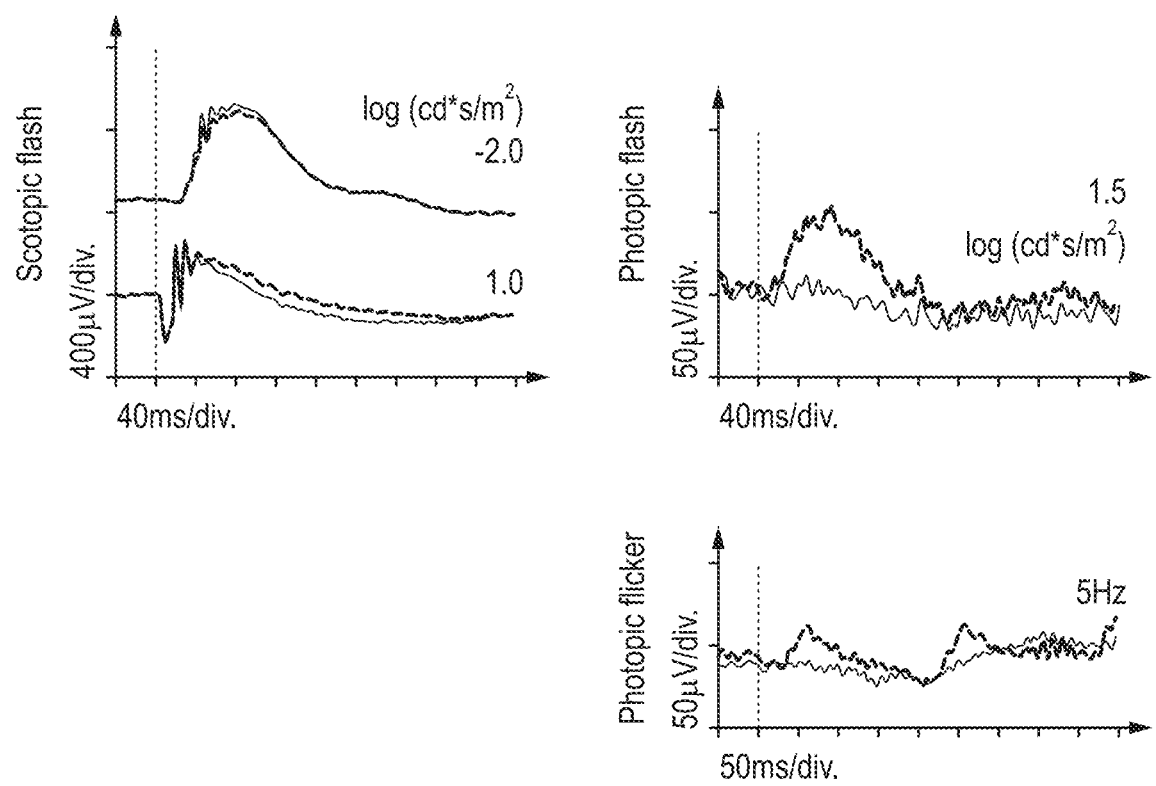
FIG. 3 shows representative ERG measurements from CNGA3-deficient mice treated on one eye with the vector according to the invention.

For representative results see FIG. 3: Representative ERG measurements from CNGA3-deficient mice treated on one eye (treated eye, black traces) with rAAV.hCNGA3 vector. The traces from the untreated control eye are shown in grey. The biological activity conferred by the rAAV.hCNGA3 vector-mediated expression of hCNGA3 is clearly evident as elevation of specific ERG components (7 Hz scotopic flicker, 5 Hz photopic flicker and photopic flash) that are mediated by cone photoreceptors and are missing in CNGA3-deficient mice.

The rAAV.hCNGA3 vector treatment resulted in a clear therapeutic effect in the treated eye reflected by elevation of specific ERG components. After completion of the ERG measurements mice were sacrificed, the eyes enucleated and processed for immunohistological analysis of hCNGA3 transgene expression (transgene expression assay, TEA). For this, the tissue was fixed and cryoembedded. Vertical cryosections were stained with a rat monoclonal antibody that binds to mouse and human CNGA3 protein. The immunosignal was detected with a Cy3 tagged donkey anti-rat IgG secondary antibody. Confocal images from the immunostained cryosections were collected using a Leica SP8 SMD confocal laser scanning microscope. The anti-CNGA3 antibody also detects mouse Cnga3 protein and gives a specific signal in cone photoreceptor outer segments of wildtype mouse retina and no signal in Cnga3-deficient retina. After treatment with rAAV.hCNGA3 vector a clear and specific signal for CNGA3 was observed in the cone photoreceptor outer segments in the treated eye, which was absent in the untreated eye.

Figure 4:
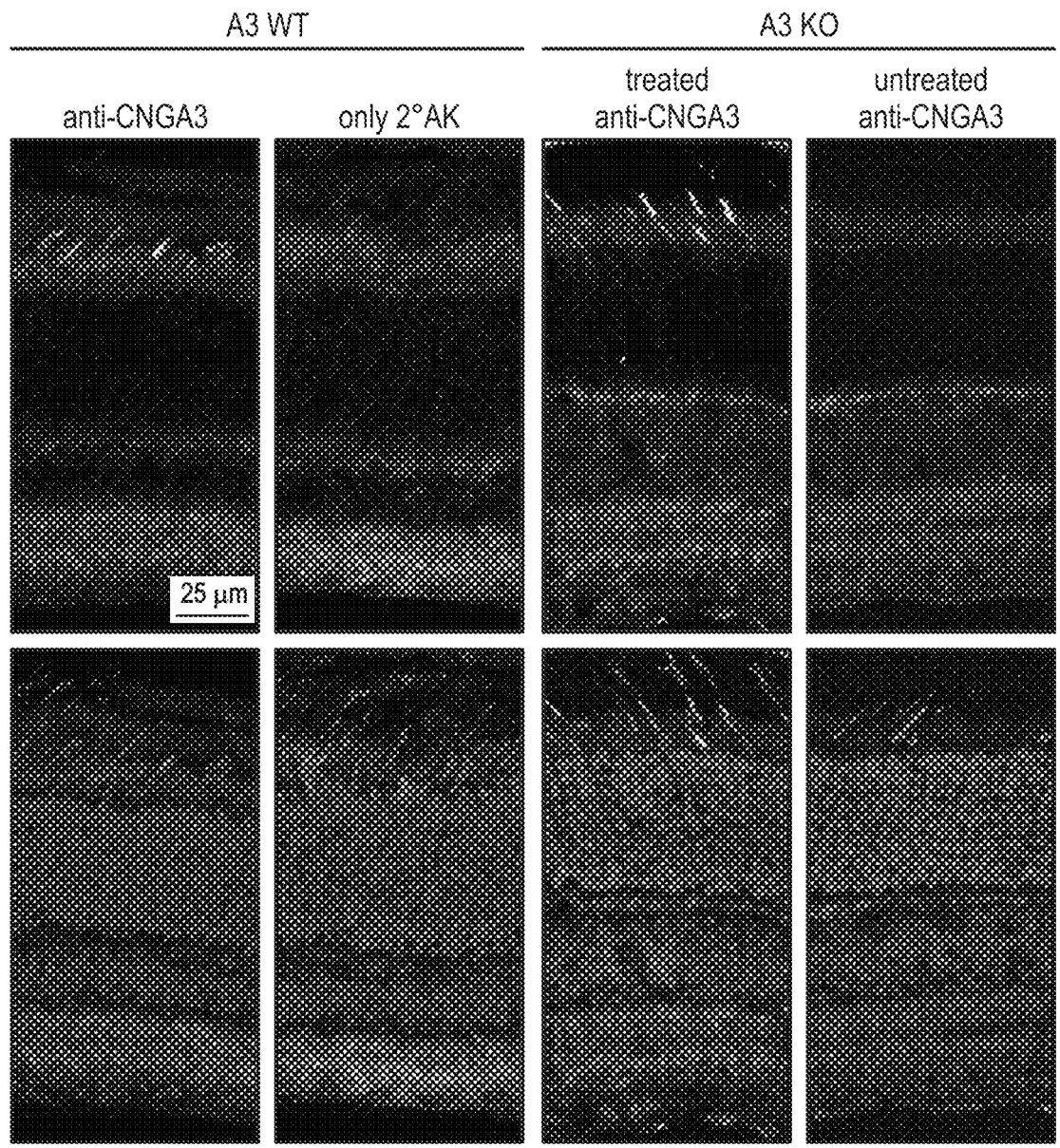
FIG. 4 depicts representative confocal images from immunohistological stainings of hCNGA3 in CNGA3-deficient mice (A3KO) treated with rAAV.hCNGA3 vector.

For representative results see FIG. 4: Representative confocal images from immunohistological stainings of hCNGA3 in CNGA3-deficient mice (A3KO) treated with the rAAV.hCNGA3 vector. The anti-CNGA3 antibody (working dilution in all experiments 1:50) also detects mouse Cnga3 protein and gives a specific signal in cone photoreceptor outer segments (rod-shaped structures in the upper part of the image) of wildtype mouse retina (left two panels) and no specific signal in the retina of untreated CNGA3-deficient mice (right two panels). The specific signal for the hCNGA3 protein encoded by the rAAV.hCNGA3 vector is shown in the third panel, which is absent in the untreated A3KO shown in the fourth panel. Panel two shows a secondary antibody only control staining. The lower panels show an overlay of the CNGA3 signal with the cone photoreceptor-specific marker peanut agglutinin and the nuclear dye Hoechst 4322.

In conclusion, the rAAV.hCNGA3 vector expresses the hCNGA3 transgene efficiently and specifically in cone photoreceptors of CNGA3-deficient mice and confers cone-mediated vision to these mice that lack cone function from birth (biological activity).

4. AAV8 Biodistribution and Shedding after Subretinal Injection in Non-Human Primates In another study the virus distribution and shedding was analysed after a single subretinal administration of clinical grade recombinant adeno-associated virus (rAAV) in non-human primates. This is important for an environmental risk assessment of the gene therapeutic method according to the invention.

18 non-human primates (*Macacca fascicularis*) underwent 23G pars plana vitrectomy and subretinal injection in three cohorts (high dose: $1\times10^{12}$ vector genomes [vg], low dose: $1\times10^{11}$ vg, or vehicle only). Four additional animals received intravitreal injections to mimic via falsa biodistribution. Tissues samples were harvested at necropsy (day 91) from the treated eye, draining lymph nodes, salivary gland and spleen, optic nerve, brain and spinal cord, heart, lung, liver, adrenal glands and gonads. Blood, urine, lacrimal and nasal swabs were harvested from each animal prior to dosing and 1, 2 and 3 days and 1, 4 and 13 weeks after application of the vector for DNA extraction and quantification of vector genomes by qPCR.

Dose dependent rAAV DNA was found in the treated retina and optic nerve. Quantifiable levels of rAAV DNA were also detected in optic chiasm of 2 animals of the high dose group. Transient shedding was found in all bio fluids. The highest concentrations were found in lacrimal fluid of the high dose group. DNA was not detected in the germ line tissues and apart from sporadic signals detected in a small number of animals in the lymph nodes and spleen, all remaining tissues were negative. Blood samples showed quantifiable levels of rAAV vector DNA at 24 and 72 hours after treatment, but were negative at all other time points tested.

These data are relevant for the clinical implementation of the invention, where trial subjects, investigators and regulators alike are interested to identify environmental risks associated with application of genetically modified organisms. While shedding into biofluids seems to occur in a dose dependent manner, transduction of off-target organs seems minimal.

5. Humoral Immune Response to Subretinal AAV8 in Non-Human Primates

Knowledge of the humoral immune response to single subretinal administration of clinical grade recombinant adeno-associated virus (rAAV) in non-human primates is a key factor for the development of safe and efficient clinical trial protocols for the retinal gene therapy according to the invention. For this reason the inventors explored anti-drug-antibody (ADA) titres in non-human primates (*Macacca fascicularis*) after single subretinal administration of a rAAV8-pseudotyped virus.

18 monkeys received subretinal injections in three cohorts (high dose: $1\times10^{12}$ vector genomes [vg], low dose: $1\times10^{11}$ vg, or vehicle only) and concomitant immunosuppressive therapy equivalent to a clinical trial scenario. Four additional animals received intravitreal injections to mimic biodistribution e.g. after surgical complications. Baseline samples were compared to those taken 1, 2 and 3 days and 1, 4 and 13 weeks after application of the vector.

The anti-drug-antibody (ADA) titres in all animals of the low dose group stayed constant over the 13 week observation period. The subretinal high dose group showed greatest variability over time, but no clear pattern of humoral immune response.

This study provides data relevant for a clinical application of the invention, where rAAV8 might be used for subretinal delivery of the hCNGA3 transgene. When mimicking the clinical scenario with clinical grade vector, surgery and concomitant immunosuppression, no induction of anti-drug-antibodies occurred in non-human primates.

6. Successful Delivery of rAAV8.CNGA3 in a Patient with CNGA3 Based Achromatopsia The aim of this clinical interventional study (NCT02610582) was to test safety aspects of the AAV8 based supplementation gene therapy according to the invention in patients with CNGA3 based achromatopsia.

After extensive safety testing in a dose escalation study in 34 non-human primates (NHP) the inventors selected a dosing range of $1\times10^{10}$, $5\times10^{10}$, and $1\times10^{11}$ vector genomes (vg) for an exploratory, dose-escalation clinical phase I/II trial. A total of 9 patients with homozygous or compound heterozygous mutations in CNGA3 received a single subretinal injection of either $1\times10^{10}$ vg (n=3), $5\times10^{10}$ vg (n=3), or $1\times10^{11}$ vg (n=3) each in 0.2 ml balanced salt solution. Concomitant steroid treatment (Prednisolone 1 mg/kg/d) was initiated 1 day prior surgery. The primary endpoint—safety of application—was assessed by clinical examination and best corrected visual acuity (BCVA).

NHP safety data showed no persisting test item-related changes after application of $\leq 1\times10^{12}$ vg 90 days after dosing. In the clinical trial, all patients received the respective dose ($1\times10^{10}$-$1\times10^{11}$ vg) safely and without surgical or post-surgical complications such as retinal detachment, hemorrhage or inflammation unresponsive to treatment. BCVA reached baseline levels as soon as 14 days post treatment. Structural changes at the level of the retinal pigment epithelium and inner/outer photoreceptor segments were attributed to the surgical procedure (see above).

The NHP safety study showed that $\leq 1\times10^{12}$ vg can be applied without relevant sequelae. This was the first clinical application of AAV8 mediated subretinal gene therapy in the eye. The application was well tolerated and did not lead to clinically apparent inflammation under concomitant Prednisolone treatment. Even though the application involved macular detachment, visual acuity reached baseline levels within 14 days.

7. Safety after Subretinal Delivery of AAV8.hCNGA3 in Patients with Achromatopsia Safety as the primary endpoint was assessed by clinical examination of ocular inflammation (slit lamp, fundus biomicroscopy, angiography, perimetry or electrophysiology). At the current stage (15 months into the trial) with all patients having been treated and followed up for minimum of three months, not a single serious adverse event had to be documented. Additionally, there was not a single ocular adverse event, which required additional action and no non-ocular adverse events, which were not resolved without sequelae. Generally, this reflects the excellent safety profile already seen in the pre-clinical toxicology study in NHPs.

8. Efficacy after Subretinal Delivery of AAV8.hCNGA3 in Patients with Achromatopsia Although not representing a main goal of this safety study, explorative efficacy endpoints were chosen to screen for their suitability in future efficacy studies. These included best corrected visual acuity, patient reported outcome measures and others.

One of the most relevant endpoints in ocular clinical trials is the best corrected visual acuity. In this endpoint, all available data at this time-point of submission of this document indicate no sustained and/or substantial deleterious effect of the treatment. While the surgery can lead to transient reduction of visual acuity (as expected), all patients with a follow up of at least 6 months show improvement in visual acuity and all patients with a follow up of 12 months continue to show also improvement in visual acuity. This is illustrated by the graphs depicted in FIG. 5, top (A) for the treated eye, bottom (B) for the untreated eye.

Patient reported outcome measures gain importance in trial protocols as they typically reflect parameters important for our patients' quality of life. Interim results of the ongoing trial (NCT02610582) demonstrate that the vast majority of the study patients reported a fast and relevant improvement of their key symptom glare after subretinal injection of rAAV.hCNGA3. The majority also reported an improvement in recognition of letters and numbers and in their fixation ability. These preliminary results were found distributed quite homogenously in all three dosage groups.

Ganzfeld stimulation and functional magnetic resonance (fMRI) imaging was used to quantify localized metabolic activity in the visual cortex dependent on stimuli originating from the treated area and the cone photoreceptor system. Three groups of three patients each were treated with low-, medium- or high-dose of AAV8.hCNGA3 gene therapy in the study eye to restore local cone function. fMRI was performed before and at three months after the treatment.

Figure 6A:
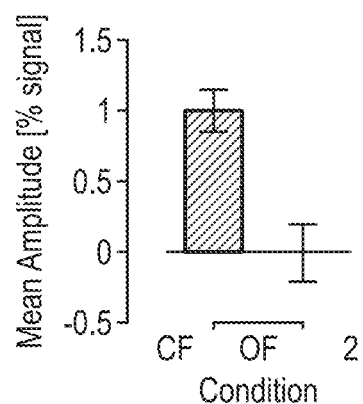
FIGS. 6A-6B depict the change in metabolic peak activity in the visual cortex after treatment with AAV8.hCNGA3 (example). Before treatment (6A), this achromatic patient responded to a luminance contrast pattern (left column), but not to an isoluminant chromatic contrast pattern (right column=0). After treatment, the isoluminant chromatic signal (6B, right column) reached similar levels as after luminance contrast stimulation.
Figure 6B:
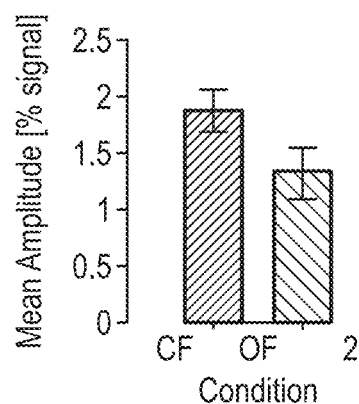
Figure 6C:
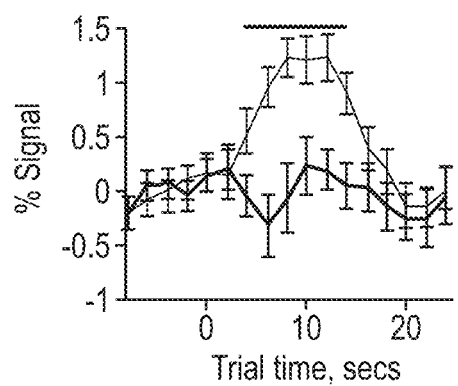
FIGS. 6C-6D depict fMRI signals from the same patient, resolved over time after stimulus presentation. Grey lines present signal amplitude in response to contrast stimuli; blue lines in response to isoluminant chromatic contrast stimuli. Before treatment (FIG. 6C) chromatic stimuli do not produce increase in fMRI signal amplitude, after treatment (FIG. 6D) signal amplitude is clearly increased.
Figure 6D:
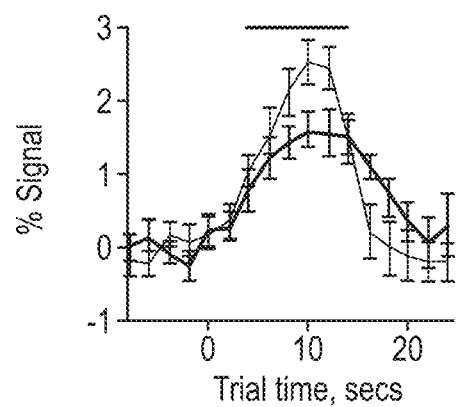

This allowed us to assess the (re)organization of the visual cortex as well the whole brain network at these time-points, and to compare with the corresponding responses we collected from normal-trichromatic subjects. In each fMRI session the subjects performed three visual stimulation experiments under mesopic light conditions: a) retinotopic mapping, b) isoluminant color contrast (not resolved by achromatic retinae) vs luminance contrast, and c) spatial frequency gratings (0.3, 1, 5 cycles per degree) at low (3%) and high (50%) contrast. For all patients, the baseline response before the treatment was, as expected, much higher for luminance contrast (grey columns on the left in FIG. 6A) in comparison to isoluminant chromatic stimuli (on the right in FIG. 6A) that gave very weak to no response. In comparison with the control group all responses were lower and slower. Three months after, a general increase of the signal was observed in all cases. Importantly, in some subjects from the medium-, and high-dose groups (blue column on the right of FIG. 6B), the amplitude of the MRI signals reached levels similar to those observed in response to luminance contrast stimulation (grey column on the left of FIG. 6B). FIG. 6C (before treatment) and 6D (after treatment) show similar data as 6A and 6B, respectively; however, here the fMRI signals are resolved over time (in s) after presenting the stimuli (contrast stimulus in grey, isoluminant colour stimuli in blue). The peak of the signal is reached after approximately 10 s. patients (representative case from the intermediate dose group).

An increase of the responses to intermediate and higher spatial frequencies was also observed (not shown). These results are an indication of brain activation with isoluminant chromatic stimuli not resolved without cone function and also point to brain plasticity after AAV8.hCNGA3 gene therapy and provide the first evidence of successfully activating cone-related brain pathways in these patients (representative case from the intermediate dose group).

9. Nucleic Acid Sequences

The following nucleotide and amino acid sequences are identified in the sequence listing.

hArr3 promoter nucleotide sequence: SEQ ID No. 1
hCNGA3 nucleotide sequence: SEQ ID No. 2
hCNGA3 amino acid sequence: SEQ ID No. 3
WPREm nucleotide sequence: SEQ ID No. 4
BGH pA nucleotide sequence: SEQ ID No. 5
L-ITR nucleotide sequence: SEQ ID No. 6
R-ITR nucleotide sequence: SEQ ID No. 7

What is claimed is:

1. A polynucleotide, comprising
a transgene expression cassette, comprising
   (a) a nucleic acid encoding the promoter of human retinal arrestin 3 gene (hArr3);
   (b) a nucleic acid encoding the human cone cyclic nucleotide-gated channel alpha 3 subunit (hCNGA3) or fragments thereof exhibiting hCNGA3 activity, and
   (c) a nucleic acid encoding regulatory elements necessary for effective expression of hCNGA3.

2. The polynucleotide of claim 1, wherein said regulatory elements comprise
   (c1) a woodchuck stomatitis virus posttranscriptional regulatory element (WPRE).

3. The polynucleotide of claim 2, wherein said WPRE is a mutated WPRE (WPREm), said WPREm comprising non-expressible woodchuck hepatitis virus X protein (WHX) open reading frame (WHX OR).

4. The polynucleotide of any of claim 1, wherein said regulatory elements comprise
   (c2) a polyadenylation signal (pA).

5. The polynucleotide of claim 4, wherein said pA is a bovine growth hormone pA (BGH pA).

6. The polynucleotide of claim 1, wherein it further comprises a nucleic acid encoding inverted terminal repeats (ITRs) flanking said transgene expression cassette, wherein at least one ITR is adjacent to said hArr3 promoter (L-ITR) and at least one ITR is adjacent to said pA (R-ITR).

7. The polynucleotide of claim 6, wherein said ITRs are derived from AAV serotype 2 (ITR AAV2).

8. The polynucleotide of claim 1 comprising an arrangement order selected from the following group:
   (a)-(b)-(c), (a)-(b)-(c1)-(c2), and (L-ITR)-(a)-(b)-(c1)-(c2)-(R-ITR).

9. The polynucleotide of claim 1, wherein said nucleic acid encoding the promoter of hArr3 comprises the nucleotide sequence of SEQ ID No. 1.

10. The polynucleotide of claim 1, wherein said nucleic acid encoding hCNGA3 comprises the nucleotide sequence of SEQ ID No. 2 or a nucleotide sequence encoding the amino acid sequence of SEQ ID No. 3.

11. The polynucleotide of claim 3, wherein said nucleic acid encoding WPREm comprises the nucleotide sequence of SEQ ID No. 4.

12. The polynucleotide of claim 5, wherein said nucleic acid encoding BGH pA comprises the nucleotide sequence of SEQ ID No. 5.

13. The polynucleotide of claim 6, wherein said nucleic acid encoding L-ITR comprises the nucleotide sequence of SEQ ID No. 6 and/or said nucleic acid encoding R-ITR comprises the nucleotide sequence of SEQ ID No. 7.

14. A nucleic acid vector comprising a polynucleotide comprising a transgene expression cassette, comprising
   (a) a nucleic acid encoding the promoter of human retinal arrestin 3 gene (hArr3);
   (b) a nucleic acid encoding the human cone cyclic nucleotide-gated channel alpha 3 subunit (hCNGA3) or fragments thereof exhibiting hCNGA3 activity, and
   (c) a nucleic acid encoding regulatory elements necessary for effective expression of hCNGA3.

15. The nucleic acid vector of claim 14, which is a circular plasmid further comprising a backbone having a length of ≥5,000 bp or ≥5,500 bp.

16. The nucleic acid vector of claim 15, wherein said backbone comprises 0 to ≤5 open reading frames (ORFs).

17. The nucleic acid vector of claim 15, wherein said backbone comprises a selection marker selected from the group consisting of: an antibiotic resistance encoding nucleic acid and a kanamycin resistance encoding nucleic acid (KanR).

18. The nucleic acid vector of claim 17, wherein said selection marker is at its 5' and 3' termini remotely spaced apart from the polynucleotide by ≥1,900 bp.

19. The nucleic acid vector of claim 15, wherein said backbone comprises 0 to ≤10 restriction enzyme recognition sites (RERSs).

20. The nucleic acid vector of claim 15, wherein said backbone comprises 0 to ≤5 promoters.

21. The nucleic acid vector of claim 15, wherein said backbone further comprises a pUC18 origin of replication (ORI) ORI.

22. The nucleic acid vector of claim 15, wherein said backbone comprises the nucleotide sequence of SEQ ID No. 8.

23. The nucleic acid vector of claim 15, wherein the vector is an adeno-associated viral (AAV) vector.

24. The nucleic acid vector of claim 23, wherein the serotype of the AAV capsid sequence of said AAV vector is selected from the group consisting of: AAV2, AAV5, AAV8, and combinations thereof.

25. A pharmaceutical preparation comprising the nucleic acid vector of claim 15, and a pharmaceutically acceptable carrier.

26. The pharmaceutical preparation of claim 25, wherein said pharmaceutically acceptable carrier is selected from the group consisting of: saline solution, balanced sterile saline solution, surfactant, and micronized poloxamer.

27. A method of making a recombinant adeno-associated viral (rAAV) vector comprising inserting into an adeno-associated viral vector the polynucleotide of claim 1.

28. The method of claim 27, wherein said recombinant adeno-associated viral vector is a nucleic acid vector comprising a polynucleotide, comprising a transgene expression cassette, comprising
   (a) a nucleic acid encoding the promoter of human retinal arrestin 3 gene (hArr3);
   (b) a nucleic acid encoding the human cone cyclic nucleotide-gated channel alpha 3 subunit (hCNGA3) or fragments thereof exhibiting hCNGA3 activity, and
   (c) a nucleic acid encoding regulatory elements necessary for effective expression of hCNGA3.

29. A method for treating a disease associated with a genetic mutation that affects retinal cone cells, wherein the method comprises administering to a subject in need of such treatment the nucleic acid vector of claim 14, thereby treating the subject.

30. The method of claim 29, wherein the disease is achromatopsia (ACHM).

31. The method of claim 29, wherein the disease is achromatopsia type 2 (ACHM2).

32. The method of claim 29, wherein the vector is administered subretinally or intravitreally.

* * * * *

SEQUENCE LISTING

```
<160> NUMBER OF SEQ ID NOS: 8

<210> SEQ ID NO 1
<211> LENGTH: 405
<212> TYPE: DNA
<213> ORGANISM: Artificial Sequence
<220> FEATURE:
<223> OTHER INFORMATION: hArr3 Promoter Nucleotide Sequence

<400> SEQUENCE: 1
aacacaaagg cctatacttt gagccctccc atttcaatcc cccaccatgc ttcacctttc      60
agacctccaa ctccactttg atcccagttc tcaggttcaa ggcctcacaa ggccaaaatc     120
ctgaagttac ccttctcaaa ctcccttgcc tttaacatca tcagaatcaa cctcctaccc     180
ccactctgtc ccagcagcaa tagcctgcta atcttttagc cactaatctt ttaggcacta     240
atctgctttc caaactcttg gcacctgaac tatttatagc agtgttttat gcccccccac     300 caagaacccct attcttttcc catgaccccc accaatcaaa acactcagag gactgtgggt     360
ataagaggct ggggaggcag gcatagcaac cagagctgga gactg                     405

<210> SEQ ID NO 2
<211> LENGTH: 2085
<212> TYPE: DNA
<213> ORGANISM: Artificial Sequence
<220> FEATURE:
<223> OTHER INFORMATION: hCNGA3 Nucleotide Sequence

<400> SEQUENCE: 2
atggccaaga tcaacaccca atactcccac ccctccagga cccacctcaa ggtaaagacc      60
tcagaccgag acctcaatcg cgctgaaaat ggcctcagca gagcccactc gtcaagtgag     120
gagacatcgt cagtgctgca gccggggatc gccatggaga ccagaggact ggctgactcc     180
gggcagggct ccttcaccgg ccaggggatc gccaggctgt cgcgcctcat cttcttgctg     240
cgcaggtggg ctgccaggca tgtgcaccac caggaccagg gaccggactc tttttcctgat     300 cgtttccgcg gagccgagct taaggaggtg tccagccaag aaagcaatgc ccaggcaaat     360
gtgggcagcc aggagccagc agacagaggg agaagcgcct ggcccctggc caaatgcaac     420
```

```
actaacacca gcaacaacac ggaggaggag aagaagacga aaaagaagga tgcgatcgtg    480
gtggacccgt ccagcaacct gtactaccgc tggctgaccg ccatcgccct gcctgtcttt    540
tataactggt atctgcttat ttgcagggcc tgtttcgatg agctgcagtc cgagtacctg    600
atgctgtggc tggtcctgga ctactcggca gatgtcctgt atgtcttgga tgtgcttgta    660
cgagctcgga caggttttct cgagcaaggc ttaatggtca gtgataccaa caggctgtgg    720
cagcattaca agacgaccac gcagttcaag ctggatgtgt tgtccctggt ccccaccgac    780
ctggcttact aaaggtggg cacaaactac ccagaagtga ggttcaaccg cctactgaag    840 tttttcccggc tctttgaatt ctttgaccgc acagagacaa ggaccaacta ccccaatatg    900
ttcaggattg ggaacttggt cttgtacatt ctcatcatca tccactggaa tgcctgcatc    960
tactttgcca tttccaagtt cattggtttt gggacagact cctgggtcta cccaaacatc   1020
tcaatcccag agcatgggcg cctctccagg aagtacattt acagtctcta ctggtccacc   1080
ttgaccctta ccaccattgg tgagacccca cccccgtga aagatgagga gtatctcttt   1140
gtggtcgtag acttcttggt gggtgttctg attttttgcca ccattgtggg caatgtgggc   1200
tccatgatct cgaatatgaa tgcctcacgg gcagagttcc aggccaagat tgattccatc   1260
aagcagtaca tgcagttccg caaggtcacc aaggacttgg agacgcgggt tatccggtgg   1320
tttgactacc tgtgggccaa caagaagacg gtggatgaga aggaggtgct caagagcctc   1380
ccagacaagc tgaaggctga gatcgccatc aacgtgcacc tggacacgct gaagaaggtt   1440
cgcatcttcc aggactgtga ggcagggctg ctggtggagc tggtgctgaa gctgcgaccc   1500
actgtgttca gccctgggga ttatatctgc aagaagggag atattgggaa ggagatgtac   1560
atcatcaacg agggcaagct ggccgtggtg gctgatgatg gggtcaccca gttcgtggtc   1620
ctcagcgatg gcagctactt cggggagatc agcattctga acatcaaggg gagcaagtcg   1680
gggaaccgca ggacggccaa catccgcagc attggctact cagacctgtt ctgcctctca   1740
aaggacgatc tcatggaggc cctcaccgag taccccgaag ccaagaaggc cctggaggag   1800
aaaggacggc agatcctgat gaaagacaac ctgatcgatg aggagctggc cagggcgggc   1860
gcggacccca aggaccttga ggagaaagtg gagcagctgg ggtcctccct ggacaccctg   1920
cagaccaggt ttgcacgcct cctggctgag tacaacgcca cccagatgaa gatgaagcag   1980
cgtctcagcc aactggaaag ccaggtgaag ggtggtgggg acaagcccct ggctgatggg   2040
gaagttcccg gggatgctac aaaaacagag gacaaacaac agtga               2085
```

<210> SEQ ID NO 3
<211> LENGTH: 694
<212> TYPE: PRT
<213> ORGANISM: Artificial Sequence
<220> FEATURE:
<223> OTHER INFORMATION: hCNGA3 Amino Acid Sequence

<400> SEQUENCE: 3

```
Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60
```

```
Phe Thr Gly Gln Gly Ile Ala Arg Leu Ser Arg Leu Ile Phe Leu Leu
 65                  70                  75                  80

Arg Arg Trp Ala Ala Arg His Val His His Gln Asp Gln Gly Pro Asp
                 85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
130                 135                 140

Asn Asn Thr Glu Glu Glu Lys Lys Thr Lys Lys Lys Asp Ala Ile Val
145                 150                 155                 160

Val Asp Pro Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
        290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
            340                 345                 350

Ile Tyr Ser Leu Tyr Trp Ser Thr Leu Thr Leu Thr Thr Ile Gly Glu
        355                 360                 365

Thr Pro Pro Pro Val Lys Asp Glu Glu Tyr Leu Phe Val Val Val Asp
        370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
            420                 425                 430

Leu Glu Thr Arg Val Ile Arg Trp Phe Asp Tyr Leu Trp Ala Asn Lys
        435                 440                 445

Lys Thr Val Asp Glu Lys Glu Val Leu Lys Ser Leu Pro Asp Lys Leu
        450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
```

```
            485                 490                 495
Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
            515                 520                 525

Val Val Ala Asp Asp Gly Val Thr Gln Phe Val Val Leu Ser Asp Gly
            530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
            565                 570                 575

Phe Cys Leu Ser Lys Asp Leu Met Glu Ala Leu Thr Glu Tyr Pro
            580                 585                 590

Glu Ala Lys Lys Ala Leu Glu Glu Lys Gly Arg Gln Ile Leu Met Lys
            595                 600                 605

Asp Asn Leu Ile Asp Glu Glu Leu Ala Arg Ala Gly Ala Asp Pro Lys
            610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                        645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
            675                 680                 685

Thr Glu Asp Lys Gln Gln
            690

<210> SEQ ID NO 4
<211> LENGTH: 543
<212> TYPE: DNA
<213> ORGANISM: Artificial Sequence
<220> FEATURE:
<223> OTHER INFORMATION: WPREm nucleotide sequence

<400> SEQUENCE: 4
aatcaacctc tggattacaa atttgtgaaa gattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact     240 ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaagctga cgtcctttcc agggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cga                                                                   543

<210> SEQ ID NO 5
<211> LENGTH: 208
<212> TYPE: DNA
<213> ORGANISM: Artificial Sequence
<220> FEATURE:
<223> OTHER INFORMATION: BGH pA Nucleotide Sequence
```

```
<400> SEQUENCE: 5
ctgtgccttc tagttgccag ccatctgttg tttgcccctc ccccgtgcct tccttgaccc      60
tggaaggtgc cactcccact gtcctttcct aataaaatga ggaaattgca tcgcattgtc     120
tgagtaggtg tcattctatt ctgggggtg gggtggggca ggacagcaag ggggaggatt      180
gggaagacaa tagcaggcat gctgggga                                        208

<210> SEQ ID NO 6
<211> LENGTH: 130
<212> TYPE: DNA
<213> ORGANISM: Artificial Sequence
<220> FEATURE:
<223> OTHER INFORMATION: L-ITR Nucleotide Sequence

<400> SEQUENCE: 6
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 7
<211> LENGTH: 130
<212> TYPE: DNA
<213> ORGANISM: Artificial Sequence
<220> FEATURE:
<223> OTHER INFORMATION: R-ITR Nucleotide Sequence

<400> SEQUENCE: 7
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc      120 gagcgcgcag                                                            130

<210> SEQ ID NO 8
<211> LENGTH: 5591
<212> TYPE: DNA
<213> ORGANISM: Artificial Sequence
<220> FEATURE:
<223> OTHER INFORMATION: pGL2.KanR Vector Backbone Nucleotide Sequence

<400> SEQUENCE: 8
tgggcctcag tgagcgagcg agcgcgcagc tgcattaatg aatcggccaa cgcgcgggga      60
gaggcggttt gcgtattggg cgctcttccg cttcctcgct cactgactcg ctgcgctcgg     120
tcgttcggct gcggcgagcg gtatcagctc actcaaaggc ggtaatacgg ttatccacag     180
aatcagggga taacgcagga aagaacatgt gcgcgttgctg gcgtttttcc ataggctccg     240 ccccccctgac gagcatcaca aaaatcgacg ctcaagtcag aggtggcgaa acccgacagg     300
actataaaga taccaggcgt ttccccctgg aagctccctc gtgcgctctc ctgttccgac     360
cctgccgctt accggatacc tgtccgcctt tctcccttcg ggaagcgtgg cgctttctca     420
tagctcacgc tgtaggtatc tcagttcggt gtaggtcgtt cgctccaagc tgggctgtgt     480
gcacgaaccc cccgttcagc ccgaccgctg cgccttatcc ggtaactatc gtcttgagtc     540
caacccggta agacacgact tatcgccact ggcagcagcc actggtaaca ggattagcag     600
agcgaggtat gtaggcggtg ctacagagtt cttgaagtgg tggcctaact acggctacac     660
tagaagaaca gtatttggta tctgcgctct gctgaagcca gttaccttcg gaaaaagagt     720
tggtagctct tgatccggca aacaaaccac cgctggtagc ggtggttttt ttgtttgcaa     780
gcagcagatt acgcgcagaa aaaaaggatc tcaagaagat cctttgatct tttctacggg     840
```

```
gtctgacgct cagtggaacg aaaactcacg ttaagggatt ttggtcatga ctgtggaatg    900
tgtgtcagtt aggcgacata ggtgatctat gtagaagcct agtggaacag gttagtttga    960
gtagctttag aatgtaaatt ctgggatcat agtgtagtaa tctctaatta acggtgacgg   1020
tttgtaagac aggtcttcgc aaaatcaagc ggcaggtgat ttcaacagat tcttgctgat   1080
ggtttaggcg tacaatgccc tgaagaataa gtaagagaat agcactcctc gtcgcctaga   1140
attacctacc ggcgtccacc ataccttcga ttatcgcgcc cactctccca ttagtcggca   1200
caggtggatg tgttgcgata gcccgctaag atattctaag gcgtaacgca gatgaatatt   1260
ctacagagtt gccataggcg ttgaacgctt cacggacgag aggaatgttg cgtatagagc   1320
gtgagtcatc gaagtggtgt atacactcgt acttaacatc tagcccggct ctatcagtac   1380
accagtgcct tgaatgacat actcatcatt aaactttctc aacagtcaaa cgaccaagtg   1440
catttccaag gagtgcgaag gagattcatt ctctcgccag cactgtaata ggcactaaaa   1500
gagtgaagat aagctagagt gccgtgctaa gacggtgtcg gaacaaagcg gtcttacggt   1560
cagtcgtatt tcctgtcgag tcccgtccag ttgagcgtat cactcccagt gtactagcaa   1620
gccgagaagg ctgtgcttgg agtcaatcgg atgtaggatg gtctccagac accgggccac   1680
cactcttcac gcctagaagc atagaacgtc gagcagacat caaagtctta gtaccggacg   1740
tgccgtttca ctgcgaatat tacctgaagc tgtaccgtta ttgcggagca aagtgacagt   1800
gctgctctta tcatatttgt attgacgaca gccgccttcg cggtttcctc agactctaga   1860
tcgaatacag gcttattgta ggcagaggca cgcccttgtt agtggctgcg gcaatatctt   1920
ccgatcccct tgtctaacca tgaatcaatt ctctcatttg aagacctaa tatgtcatca    1980 ttagtgtttc aaatgccacc aaataccgcc tagaaatgtc tatgatgtgt gtccactaga   2040
agttgattca caaacgactg ctagaatcgc gtgatagggc atcttgaagt ttacattgtt   2100
gtatcgcaag gtactccgat cttaatggat gcgaagtggt acggatgcaa tcaagcgcgt   2160
gagagcggta cattagagcg ttcacctacg ctacgctaac gggcgattct gataagaatg   2220
cacattgcgt cgattcataa gatgtctcga ccgcatgcgc aacttgtgaa gtgtctacta   2280
tccctaagcg catatctcgc acagtaaccg aatatgtcgg catctgatgt taccgttgag   2340
ttagtgttca gctcacggaa cttattgtat gagtagagat ttgtaagagc tgttagttag   2400
ctcgctcagc taatagttgc ccacacaacg tcaaattaga gaacggtcgt aacattatcg   2460
gtggttctct aactactatc agtacccacg actcgactct gccgcagcta ggtatcgcct   2520
gaaagccagt cagcgttaag gagtgctctg accaggacaa caggcgtagt gagagttact   2580
tgttcgttgc tcttccgact cggacctgag ttcgccaacg acccacttga ggtctgagcc   2640
ggtgaagaga agtaagcatc tcgttcgcag cttgccagca ctttcagaac atgacccta    2700 tttgtttatt tttctaaata cattcaaata tgtatccgct catgagacaa taaccctgat   2760
aaatgcttca ataatattga aaaggaaga gtggccgcct cggcctaggc ttttgcaaag   2820
atcgatcaag agacaggatg aggatcgttt cgcatgattg aacaagatgg attgcacgca   2880
ggttctccgg ccgcttgggt ggagaggcta ttcggctatg actgggcaca acagacaatc   2940
ggctgctctg atgccgccgt gttccggctg tcagcgcagg ggcgcccggt tctttttgtc   3000
aagaccgacc tgtccggtgc cctgaatgaa ctgcaagacg aggcagcgcg gctatcgtgg   3060
ctggccacga cggcgttcc ttgcgcagct gtgctcgacg ttgtcactga agcgggaagg    3120
gactggctgc tattgggcga agtgccgggg caggatctcc tgtcatctca ccttgctcct   3180
```

```
gccgagaaag tatccatcat ggctgatgca atgcggcggc tgcatacgct tgatccggct    3240
acctgcccat tcgaccacca agcgaaacat cgcatcgagc gagcacgtac tcggatggaa    3300
gccggtcttg tcgatcagga tgatctggac gaagagcatc aggggctcgc gccagccgaa    3360
ctgttcgcca ggctcaaggc gagcatgccc gacggcgagg atctcgtcgt gacccatggc    3420
gatgcctgct tgccgaatat catggtgaaa atggccgct tttctggatt catcgactgt     3480
ggccggctgg gtgtggcgga ccgctatcag gacatagcgt tggctacccg tgatattgct    3540
gaagagcttg gcggcgaatg ggctgaccgc ttcctcgtgc tttacggtat cgccgctccc    3600
gattcgcagc gcatcgcctt ctatcgcctt cttgacgagt tcttctgagg taccatgatg    3660
cgtgcatggt agaatgactc ttgataacgg acttcgacta ggcaatatcc cttgtcaact    3720
tgtcgaggag aaaagtattg actgaagcgc tcccggcaca acggccaaag aagtctcagc    3780
aatgttctta tttccgaatg acatgcgtct ccttgcgggt aaatcgccga ccgcaaaact    3840
taggagccag gatacagata ggtctaactt aggttaaggg agtaaatcct gggatcgttc    3900
agttgtaacc atatacttac gctggggctt ctccggcgga tgttactgtc accaaccacg    3960
agatttgaag taaacgcatg attgagcaca tagccgcgct atccgacaat ctccaaattg    4020
ataacatacc gttccatgaa ggccagaatt acttaccggc cctttccatg cgtgcgccat    4080
accgcactct gcgcttatcc gtccgagggg agagtgtgcg atcctccgtt aagatattct    4140
cacgtatgac gtagctatgt attgtgcaga ggtagcgaag gcgttgaaca cttcacagat    4200
ggtggggatt cggcaaagg gcgtgataac ttggggacta acataggcgt aaactacgat     4260
ggcaccaact caatcgcagc tcgtgcgccc tgaatcaacg tactcatctc aactgattct    4320
cggcaatcta cggagcgact tgattatcaa cacctgtcta gcagttctaa tcttctgcca    4380
acatcgtaca tagcctccaa gagattatca tacctatcgg cacagaagtg acacgacgcc    4440
gaagggtagc ggacttctgg tcaaccacaa ttccccaggg gacaggtcct gcggtgcgca    4500
tcactttgta agtgcaagca acccaagtga gcccagcctg gactgagctg gttcctgtgt    4560
caggtcgagg ctggggatga cagctcttgt aaacatagtg atcaagcgtg gcgtcgaacg    4620
gtcgagaaac tcatagtacc tcgggtagca acttactcag gttattgctt gaagctgtac    4680
tatttcagga gcgctgaagg tctcttcttc tgtagactga actcgcaagg gtcgtgaagt    4740
cggttccttc aatgcttaac aagaacaaag gcttactgtg cagactggaa cgcccatcta    4800
gcggctcgcg tcttgaatgc tcggtccect ttgtcattgc ggatacaatc catttccctc    4860
attcaccagc ttgcgaagtc tacattgagt agacgaatgc gacctagaag aggtgcgctt    4920
cagaacttgt gaggagtggt tgatgctcta tactccattt ggtgtttcgt gcatcaccgc    4980
gataggctga caagaggtct tgaacattga atagcaaggc acttccggtc tcatagaaga    5040
gagcacggga taaggtacgc gcgtggtacg ggaggatcaa ggggctacac gatagaaagg    5100
cttctccctc actcgctagg aggcaaatgc agaacgctgg ttactactac gatacgtgaa    5160
acttgtccaa cggttgccca agtgttaagg tgtctatcac cctagtgccg tttcccggag    5220
aaaacgccag gttgaatccg catttgaagc tacgatggtg aagtctgggt cgagcgcgcc    5280
gcatgttgat tgcgtgagta ggctcgacca agaaccgcta gtagcgtcgc tgtagaaata    5340
gttctcgaca gaccgtcgag tttagaaaat ggtagcagca ttgttcgcat ctcaatcaag    5400
```

```
tatggattac ggtgtttaca ctgtcctgcg gctacccatc gcctgaaatc cagctcgtgt    5460
caagccattg cctctccggg acgccgcatg aagtaactac atataccttg cacgggttga    5520
ctgcggtccg ttcagactcg accaaggaca caatccagcg atcggtgcgg gcctcttcgc    5580
tattacgcca g                                                        5591
```